US006452047B1

(12) United States Patent
Shigematsu et al.

(10) Patent No.: US 6,452,047 B1
(45) Date of Patent: Sep. 17, 2002

(54) PROCESS FOR PRODUCING HIGHLY PURE AROMATIC POLYCARBOXYLIC ACID

(75) Inventors: Ryusuke Shigematsu; Masayoshi Hayashi; Akio Hashimoto; Makoto Takagawa, all of Ibaraki-ken (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 09/577,153

(22) Filed: May 24, 2000

(30) Foreign Application Priority Data

May 26, 1999 (JP) .............................. 11-146613

(51) Int. Cl.⁷ .............................. C07C 51/42
(52) U.S. Cl. ........................................ 562/486
(58) Field of Search ........................... 562/486

(56) References Cited

U.S. PATENT DOCUMENTS 5,481,033 A     1/1996   Alms et al.
5,565,609 A  *  10/1996  Hirowatari et al.

FOREIGN PATENT DOCUMENTS

EP          0787712       8/1997
JP          50-135062     10/1975
JP          5-294891      11/1993
JP          7-118200      5/1995

OTHER PUBLICATIONS

Database WPI, Derwent Publications Ltd., An 1993–392609, Iwane Hiroshi, et al., "Production for bi–phenyl–di–carboxylic acids with improved yield" (Mitsubishi Petrochemical Co., Ltd.), Abstract for JP5–294891, Nov. 9, 1993.

* cited by examiner

Primary Examiner—Paul J. Killos
Assistant Examiner—Zachary C. Tucker
(74) Attorney, Agent, or Firm—Antonelli, Terry, Stout & Kraus, LLP

(57) ABSTRACT

Highly pure, less colored aromatic polycarboxylic acids are produced from crude aromatic polycarboxylic acids by simple procedures at low production costs. The crude aromatic polycarboxylic acid is mixed with aliphatic amine or alicyclic amine in the presence of a solvent to precipitate crystals of amine salt of aromatic polycarboxylic acid. The crystals are dissolved in water and decomposed, thereby obtaining the highly pure aromatic polycarboxylic acids.

22 Claims, No Drawings

PROCESS FOR PRODUCING HIGHLY PURE AROMATIC POLYCARBOXYLIC ACID

BACKGROUND OF THE INVENTION

1. Field of the Invention

The present invention relates to a process for producing highly pure aromatic polycarboxylic acids useful as raw materials for polyesters, polyamides and liquid crystal polymers, particularly useful for highly pure naphthalenedicarboxylic acids and highly pure biphenyldicarboxylic acids which are difficult to purify by known methods.

2. Description of the Prior Art

Aromatic polycarboxylic acids are commercially important as chemical intermediates, and have been widely used in the production of polyesters or polyamides particularly for use in manufacturing fibers, bottles and films. Among them, 2,6-naphthalenedicarboxylic acid is particularly useful as raw materials of polyethylene naphthalate (PEN) and wholly aromatic liquid crystal polymers having excellent physical properties and mechanical properties. Therefore, the demand for 2,6-naphthalenedicarboxylic acid is rapidly increasing in recent years.

The aromatic polycarboxylic acids presently used in wide industrial applications include terephthalic acid, isophthalic acid, phthalic acid, 2,6-naphthalenedicarboxylic acid, 4,4'-biphenyldicarboxylic acid, etc.

It has been known that aromatic polycarboxylic acids are produced by oxidizing polyalkyl aromatic hydrocarbons such as xylene, dialkylnaphthalene and dialkylbiphenyl with molecular oxygen in a solvent such as acetic acid in the presence of heavy metal such as Co and Mn and a bromine compound under high-temperature and high-pressure conditions. The aromatic polycarboxylic acids produced by the oxidation reaction contain oxidation intermediates such as monocarboxylic acids and aldehydes and impurities such as bromine adducts derived from catalysts, colored components with undefined structure and metals such as Co and Mn derived from the oxidation catalyst.

Such aromatic polycarboxylic acids containing these impurities are unsuitable as raw materials of polyesters or polyamides, because resins produced by polymerizing such aromatic polycarboxylic acids with alcohols or amines are deteriorated in physical or mechanical properties such as heat resistance, mechanical strength and dimensional stability. Also, crude aromatic dicarboxylic acids produced by oxidizing di-substituted aromatic hydrocarbons by molecular oxygen are usually colored yellow or black, and therefore, cannot be used directly in the applications requiring high-transparency such as bottles and films. Under these circumstances, continuous studies have been made over a long period of time to develop industrially useful processes for producing highly pure aromatic polycarboxylic acids with less coloration.

Organic compounds are purified generally by distillation, recrystallization, adsorption or combination thereof. However, since aromatic polycarboxylic acids have self-decomposition temperatures lower than their boiling points, it is impossible to purify aromatic polycarboxylic acids by distillation. In addition, since aromatic polycarboxylic acids are less soluble in solvents widely used in industrial purpose, it is not easy to purify aromatic polycarboxylic acids by recrystallization. In particular, naphthalenedicarboxylic acids and biphenyldicarboxylic acids are substantially insoluble in various solvents. For these reasons, no industrially advantageous process for the production of highly pure naphthalenedicarboxylic acids or highly pure biphenyldicarboxylic acids have been developed until now.

Thus, since aromatic polycarboxylic acids themselves are difficult to purify by recrystallization, an alternative method has been proposed, in which aromatic polycarboxylic acids are first reacted with amines to form amine salts having increased solubility, and then the amine salts are purified by crystallization or treatment with activated carbon, followed by decomposing the amine salts to obtain purified aromatic polycarboxylic acids.

Japanese Patent Application Laid-Open No. 50-135062 discloses a process in which crude naphthalenedicarboxylic acid are dissolved in an aqueous aliphatic amine solution, and the resultant solution is cooled or concentrated to crystallize amine salts; Japanese Patent Application Laid-Open No. 7-118200 discloses a process in which crude naphthalenedicarboxylic acids are dissolved in a mixed solvent of amine, alcohol and water, and the resultant solution is cooled to crystallize amine salts; Japanese Patent Application Laid-Open No. 5-294891 discloses a process in which crude biphenyldicarboxylic acids are dissolved in a mixed solvent of amine and alcohol, and the resultant solution is cooled to crystallize amine salts; U.S. Pat. No. 5,565,609 discloses a process in which amine salts of aromatic dicarboxylic acids are dissolved in water and then purified by adsorption with activated carbon, and the purified amine salts are thermally decomposed in the presence of water; and U.S. Pat. No. 5,481,033 discloses a process in which salts of aromatic dicarboxylic acid and aliphatic diamine are formed in an aqueous solvent, and then crystallized to obtain purified salts.

The known crystallization methods mentioned above require heating operations for complete dissolution of salts and cooling operations for precipitation of crystals, making the methods complicated and increasing utility costs. The treatment by activated carbon requires a large amount of activated carbon primarily for decoloring. Therefore, the above purification methods of crude aromatic polycarboxylic acids through the formation of amine salts also fail to avoid complicated operations and increased production costs.

It is an object of the present invention to provide a process for producing highly pure aromatic polycarboxylic acids with less coloration from crude aromatic polycarboxylic acids at low costs in simple and industrially facilitated manners.

SUMMARY OF THE INVENTION

As a result of extensive researches on purification of crude aromatic polycarboxylic acids in view of the above objects, the inventors have found that purified crystalline amine salt of an aromatic polycarboxylic acid is obtained by the salt-forming reaction in which a crude aromatic polycarboxylic acid is mixed with an aliphatic amine and/or an alicyclic amine in the presence of a solvent under conditions which allow a substantial part of the amine salt being formed to precipitate immediately after the amine salt-formation, thereby preventing the amine salt from completely dissolving into the solvent. The present invention has been accomplished on the basis of this finding.

Thus, the present invention relates to a process for producing a highly pure aromatic polycarboxylic acid, the process comprising a salt formation step of forming a crystalline amine salt by mixing an aromatic polycarboxylic acid with an aliphatic amine and/or an alicyclic amine in the presence of a solvent under conditions which allow a substantial part of the amine salt being formed to precipitate, thereby preventing the amine salt from completely dissolving into the solvent.

In the known purification methods by recrystallization through the formation of amine salts of aromatic polycarboxylic acids, the whole amine salts are dissolved into a solvent by heating, and then the resultant solution is cooled or concentrated to precipitate purified crystals of the amine salts. The inventors have found that all organic acid components in crude aromatic polycarboxylic acids are converted into salts merely by mixing crude aromatic polycarboxylic acids with amines in an appropriate solvent without heating, and that a substantial part of the amine salt of aromatic polycarboxylic acids, i.e., excess amine salts of aromatic polycarboxylic acids exceeding the solubility to the solvent are allowed to precipitate as purified crystals immediately after the formation, while the amine salts of impurities remain dissolved in the solvent. Namely, in the process of the present invention, the amine salts are purified without creating complete dissolution state as employed in the conventional purification methods, so that highly pure aromatic polycarboxylic acid are produced in extremely simple manner.

DETAILED DESCRIPTION OF THE INVENTION

The crude aromatic polycarboxylic acids to be purified in the present invention are polycarboxylic acids having one or more aromatic rings, for example, aromatic rings of aromatic hydrocarbons such as benzene, naphthalene and biphenyl, to which two or more carboxyl groups are bonded.

The crude aromatic polycarboxylic acids used as raw materials in the present invention are produced, but not critical, by oxidizing the above aromatic hydrocarbons having two or more carboxyl group-forming substituents by oxidation, such as alkyl groups, e.g., methyl, ethyl and isopropyl, formyl group and acetyl group, with molecular oxygen in the presence of an oxidation catalyst composed mainly of a heavy metal such as Co and Mn, and bromine.

Examples of disubstituted naphthalenes as raw materials of naphthalenedicarboxylic acid, to which the present invention is preferably applicable, include dimethylnaphthalenes, diethylnaphthalenes, diisopropylnaphthalenes, methylnaphthaldehydes, isopropylnaphthaldehydes and butyrylmethylnaphthalenes. Of these naphthalenes, 2,6-, 2,7- and 1,5-isomers are especially useful as raw materials of polyesters, urethanes or liquid crystalline polymers. Crude naphthalenedicarboxylic acids particularly produced by oxidizing dialkylnaphthalene with molecular oxygen in the presence of an oxidation catalyst contains, in addition to colored components and metals of oxidation catalyst of heavy metal and bromine, organic impurities such as formylnaphthoic acid as an oxidation intermediate, trimellitic acid as a decomposed product of naphthalene ring, brominated naphthalenedicarboxylic acid as brominated products, and naphthalenetricarboxylic acids derived from raw materials.

Examples of disubstituted biphenyls as raw materials of biphenyldicarboxylic acids include dimethylbiphenyl, diethylbiphenyl, diisopropylbiphenyl, methylformylbiphenyl and ethylformylbiphenyl. Of these biphenyls, 4,4'-isomers are especially useful as raw materials of polyesters, polyamides and liquid crystal polymers. Crude aromatic dicarboxylic acid produced by oxidizing disubstituted biphenyls with molecular oxygen in the presence of an oxidation catalyst usually contains, in addition to colored components and metals of oxidation catalyst, organic impurities such as formylbiphenylcarboxylic acid as oxidation intermediate, alkylbiphenyl carboxylic acids, and biphenylmonocarboxylic acids derived from the raw materials.

The process for the purification of crude aromatic polycarboxylic acids of the present invention basically comprises two steps of precipitating crystalline amine salts of aromatic dicarboxylic acids by mixing the crude aromatic polycarboxylic acids with amines in the presence of a solvent (hereinafter referred to merely as "salt formation step"), and decomposing the precipitated amine salts (hereinafter referred to merely as "salt decomposition step").

Examples of the aliphatic amines and the alicyclic amines (hereinafter referred to merely as "amines") used in the salt formation step of the present invention include aliphatic amines such as methylamine, dimethylamine, trimethylamine, ethylamine, diethylamine, triethylamine, propylamine, dipropylamine, tripropylamine, isopropylamine, diisopropylamine, triisopropylamine, butylamine, dibutylamine, tributylamine and 2-ethylhexylamine; and alicyclic amines such as piperidine, N-methylpiperidine, pyrrolidine, ethylene-imine and hexamethyleneimine. These amines may be used singly or in combination of two or more.

Of these amines, tertiary amines such as trimethylamine, triethylamine, tripropylamine and triisopropylamine are preferred in view of high decomposition speed of their salts with aromatic polycarboxylic acids and easiness of their recovery. Triethylamine and trimethylamine are more preferred in view of easiness of handling and availability.

The amine may be used in equivalent amount to carboxyl groups of the crude aromatic polycarboxylic acids or more. The economical amount for industrial use is preferably 1.0 to 1.2 equivalents to one equivalent of carboxyl group.

The crude aromatic polycarboxylic acids rapidly forms amine salts when reacted with the amines in the presence of a solvent having a dissolving power to the amine salts, such as water, alcohols, pyridines, amides and dimethyl sulfoxide. From the finding by the inventors, only the amine salts of aromatic polycarboxylic acids can be precipitated as purified crystals while retaining the amine salts of impurities dissolved in the solvent by appropriately selecting kind, composition and amount of the solvent to be used.

The purification via the salt-forming reaction between the crude aromatic polycarboxylic acid and the amine is carried out in the presence of a solvent having a dissolving power to the amine salt, such as water, alcohols, pyridines, amides and dimethyl sulfoxide. The amine salts usually have high solubility to water. For example, di(triethyl amine) salt of 2,6-naphthalenedicarboxylic acid exhibits a solubility of 100 g amine salt/100 g water or higher even at 25° C. Therefore, when only water is used as the solvent for the salt formation, the purification must be carried out at extremely low temperatures to achieve a high recovery of the amine salt, because a large amount of the amine salt is dissolved therein at ordinary temperature. On the contrary, the salt formation using only a specific organic solvents such as alcohols, pyridines, amides and dimethyl sulfoxide gives industrially acceptable recovery of the purified amine salt, because the solubility of the amine salt to these solvents is generally small as compared with the solubility to water. The amine salts of aromatic polycarboxylic acids are substantially insoluble in some water-soluble organic solvents such as acetone, acetonitrile and tetrahydrofuran. Therefore, the sole use of such a water-soluble organic solvent fails to form the amine salt, and even if formed, since all components including impurities are precipitated together.

Examples of the organic solvents for the salt formation step usable under water-free conditions include alcohols such as methanol, ethanol, propanol, isopropanol, butanol, 1,2-ethanediol, 1,2-propanediol, 1,3-propanediol, 1,3-butanediol, 1,4-butanediol, 2,3-butanediol, 1,5-pentanediol and glycerol; pyridines such as pyridine, α-picoline, β-picoline, γ-picoline, 2,4-lutidine and 2,6-lutidine; amides such as formamide, N-methylformamide, N,N-dimethylformamide, N,N-diethylformamide, N-methylacetamide, N,N-dimethylacetamide and N-methylpropionamide; and dimethyl sulfoxide. These organic solvents may be used singly or in combination of two or more. In view of purification efficiency and recovery of crystals, preferred are alcohols having 3 or less carbon atoms such as methanol, ethanol, propanol, isopropanol, 1,2-ethane diol, 1,2-propane diol and 1,3-propane diol, pyridines such as α-picoline, β-picoline, γ-picoline, and amides such as N,N-diethylacetamide and N,N-diethylformamide.

By using water alone or a solvent mixture of water and a water-soluble organic solvent as the solvent for the salt formation step in place of the alcohols, pyridines, amides and dimethylsulfoxide mentioned above, amine salts of aromatic polycarboxylic acids are obtained in the form of granular crystals having a relatively large particle size with high purification effect.

In addition to the high purity of the crystals themselves, since the crystals are easy to filter and can be effectively rinsed, the purification effect of the amine salts can be further enhanced.

Examples of the water-soluble organic solvents usable in combination with water in the salt formation step include, but not critical, alcohols such as methanol, ethanol, propanol, isopropanol, butanol, 1,2-ethanediol, 1,2-propanediol, 1,3-propanediol, 1,3-butanediol, 1,4-butanediol, 2,3-butanediol, 1,5-pentanediol and glycerol; ketones such as acetone and methyl ethyl ketone; amides such as formamide, methylformamide, dimethylformamide, diethylformamide, methylacetamide, dimethylacetamide and methylpropionamide; pyridines such as pyridine, α-picoline, β-picoline, γ-picoline, 2,4-lutidine and 2,6-lutidine; acetonitrile; tetrahydrofuran; dioxane; and dimethyl sulfoxide. In view of purification effect and recovery of crystals, preferred are acetone, acetonitrile, pyridine, picoline, alcohols having 3 or less carbon atoms such as methanol, ethanol, propanol, isopropanol, 1,2-ethanediol, 1,2-propanediol and 1,3-propanediol, amides such as dimethylacetamide and dimethylformamide, and more preferred are acetone, pyridine and picoline.

The purification via the salt formation without forming complete solution is novel purification different from the known methods such as distillation, recrystallization and adsorption ordinarily employed in purifying organic compounds. Any of the purification methods by distillation, recrystallization and adsorption must include a complete solution state in the course of the purification treatment. In contrast, the purification via the salt formation according to the present invention is performed without bring about a complete solution state and always performed in a slurry state containing as solid matters crude aromatic polycarboxylic acid as raw material and the amine salt of aromatic polycarboxylic acid precipitated by the salt formation. The purification effect may be somewhat comparable to that of recrystallization. However, in the purification via the salt formation, a high recovery of purified amine salts is achievable by mere mixing under stirring at ordinary temperature under ordinary pressure, and therefore, is more excellent in many points than the conventional recrystallization methods.

Unlike the known purification by recrystallization, the purification via the salt formation according to the present invention does not need a complete dissolution of the reaction system. The solubility of the amine salt varies depending upon kinds of aromatic polycarboxylic acid and amine, kind and amount of solvent, water content of a mixed solvent of water and water-soluble organic solvent, if used, and the salt-forming temperature. The recovery of the amine salt in the salt formation step is determined only by charge ratio between the raw materials and solvent, and the solubility of the amine salt to the solvent at the salt formation temperature. This enables the use of a variety of solvents even when a high recovery of the amine salt is required. Further, since the amine salt can be purified only by mixing under stirring at ordinary temperature under ordinary pressure, the purification is done by easy operations using simple apparatus. To achieve a high recovery in the known purification by recrystallization, only a limited number of solvents are usable because the solubility is required to have a large temperature-dependency. In addition, heating for dissolution and cooling for crystallization increase the purification costs and complicate apparatuses and operations.

The amount of the solvent used in the salt formation step is usually about 1 to 100 parts by weight, preferably about 3 to 30 parts by weight based on one part by weight of the crude aromatic polycarboxylic acid, though it varies depending on kinds of crude aromatic polycarboxylic acids and amines, kinds of the solvents, etc. An excessively large amount of the solvent reduces the recovery of amine salts. Too small an amount of the solvent results in low purification effect. The water content of the mixed solvent of water and the water-soluble organic solvent is 1 to 80% by weight, preferably 5 to 50% by weight. When the water content is too large, the recovery of amine salts is reduced. When the water content is too small, no expected purification effect by using water is obtained. Accordingly, the amount of the solvent based on the aromatic polycarboxylic acid is selected from the above range in view of the recovery and purification degree of the amine salt as well as the operability of solid-liquid separation and the recovery of solvent.

The salt formation step may be carried out in either batch-wise or continuous manners. In both batch-wise and continuous salt formations, the crude aromatic polycarboxylic acid and the amine may be added under stirring in any order to water, the organic solvent or the mixed solvent comprising water and the water-soluble organic solvent. The amine salt is readily formed when the crude aromatic polycarboxylic acid is contacted with the amine in the solvent. When a mixed solvent with a deficient water content is used, a sufficient purification is not achieve as mentioned above. A high recovery can be attained by completing the salt formation in a mixed solvent having a high water content and subsequently adding a water-soluble organic solvent to allow the amine salt dissolved in the solvent to precipitate.

The temperature and pressure of the salt formation step varies depending upon the kind, composition and amount of the solvent used and the intended recovery of the amine salt. Since the temperature is raised due to the neutralization heat of the crude aromatic polycarboxylic acid and the amine during the salt formation, the evolved heat may be dissipated, if required. Further, since the complete dissolution is avoided in the salt formation according to the present invention, heat and pressure are not needed unless otherwise required. The salt formation is usually conducted at 0 to 200° C., preferably 0 to 70° C., and more preferably 10 to 50° C. in view of easiness of industrial applications, and under a pressure of 0 to 10 MPa·G, preferably from atmospheric pressure or 1 MPa·G or less.

The slurry produced in the salt formation step contains amine salt crystals and is then subjected to solid-liquid separation such as filtration, centrifugation and decantation to separate the slurry into amine salt crystals acid and a mother liquor containing concentrated impurities. The separated crystals are rinsed or washed after reslurried with a poor solvent to the amine salt, preferably with the organic solvent used in the salt formation step, to remove the mother liquor remaining on the crystals. The purity of crystals can be further increased by dissolving off only the outer portion of crystals at which impurities are concentrated.

The mother liquor and the washings of crystals obtained in the salt formation step contain, in addition to the solvent used, non-recovered amine salt of aromatic polycarboxylic acid and impurities. When a large amount of the amine salt remains not recovered in the mother liquor or the washings, the remaining amine salt may be partly or completely recovered to increase the overall recovery by adding a poor solvent to the amine salt or by cooling to temperatures lower than the salt formation temperature, thereby decreasing the solubility of the amine salt enough to precipitate. Also, a part or whole of the amine or organic solvent contained in the mother liquor and the washings may be separated from impurities by distillation or liquid-liquid separation method, and may be recycled to the salt formation step for reuse.

By operating the salt formation step in the manner described above, substantially all the organic impurities are removed from the crude aromatic polycarboxylic acid. Further, the colored components contained in the crude aromatic polycarboxylic acid are also sufficiently removed, crystals of highly pure amine salt with less coloration are obtained.

The colored components and the organic impurities can be removed more sufficiently by treating the amine salt with a solid adsorbent or recrystallization. The solid adsorbents may include activated carbon, activated clay, zeolite, etc., and activated carbon is most preferred due to its large decoloring power and high ability of removing the organic impurities. For example, the treatment by activated carbon powder may be carried out simultaneously with the salt formation or after the salt formation by contacting the powder with a solution of the amine salt in a solvent such as water. In industrial large-scale treatment, a continuous flow method using granular activated carbon is advantageous, in which an aqueous solution of purified amine salt from the salt formation step is filtered to remove the insolubles and introduced into an adsorption column filled with granular activated carbon where the colored components and the organic impurities are removed by adsorption. After adsorption, acid or alkaline solutions containing amines, NaOH, KOH, HCl, $HNO_3$, etc., are allowed to pass through the adsorption column for desorption and regeneration, thereby using the activated carbon repeatedly.

The purified amine salt of aromatic polycarboxylic acid obtained in the salt formation step may be recrystallized for further purification. The recrystallization may be performed by dissolving the amine salt into a solvent under heating and then cooling or concentrating the resultant solution to precipitate crystals of the amine salt, or by dissolving the amine salt in a good solvent for the amine salt such as water and then adding a poor solvent for the amine salt such as acetone and alcohols, thereby precipitating crystals of the amine salt. Although the solvent usable for the recrystallization are not necessarily the same as those used in the salt formation step, the organic solvent or the mixed solvent of water and the water-soluble organic solvent used in the salt formation step is advantageous in industrial applications. By the recrystallization of the amine salt of aromatic polycarboxylic acid obtained in the salt formation step, a highly pure amine salt having remarkably improved in decoloration and containing a less amount of organic impurities are obtained.

After dissolved in water, foreign matters, insolubilized metal impurities, etc. are removed from the amine salt of aromatic polycarboxylic acid purified in the manner described above by solid-liquid separation such as filtration, centrifugation and decantation. The object compounds, aromatic polycarboxylic acids, are obtained from aqueous solutions of corresponding amine salts by a method where an acid, such as acetic acid and hydrochloric acid, having an acidity higher than that of the object aromatic polycarboxylic acid is added to the aqueous solution of the amine slat, thereby precipitating the object aromatic polycarboxylic acid; a method where the aqueous solution is directly heated to completely distill off water and amine; or a method where the amine salt is thermally decomposed in the presence of water, thereby precipitating the object aromatic polycarboxylic acid from the aqueous solution.

In the method of adding an acid to precipitate the object aromatic polycarboxylic acid, organic acids such as acetic acid and propionic acid or inorganic acids such as sulfuric acid and hydrochloric acid may be added to the aqueous solution dissolving the amine salt to precipitate the object aromatic polycarboxylic acid. Since this method is likely to precipitate fine crystals, it is preferred to increase the grain size by conducting the precipitation at elevated temperatures of 100° C. or higher, preferably about 150° C., or by prolonging the residence time of the crystals in the reaction system. The precipitated crystals are recovered by solid-liquid separation such as filtration and centrifugation, washed with water, the organic acids used, etc., and then dried, thereby obtaining highly pure aromatic polycarboxylic acids.

In the method of directly heating the aqueous solution to decompose the amine salt, the aqueous solution is heated while stirring to decompose the amine salt and completely distill off amine concomitantly with water, thereby obtaining highly pure aromatic polycarboxylic acids.

In the method of heating the aqueous solution in the presence of water to decompose the amine salt, the aqueous solution is heated in the presence of water to decompose the amine salt and then water and amine are distilled off, thereby precipitating the aromatic polycarboxylic acid from the aqueous solution. In this method, a very small amount of the organic impurities which are not removed in the salt formation step remains dissolved in the aqueous solution as amine salts, thereby further enhancing the purification effect. Also, the decomposition of the amine salt by this method is advantageous, because the resultant aromatic polycarboxylic acids have a large particle size and are excellent in flowability and easiness of filtering.

For example, in the. above method in which the amine salt of aromatic polycarboxylic acid is thermally decomposed in the presence of water and the evolved amine is distilled off to precipitate the aromatic polycarboxylic acid, an aqueous solution of the amine salt is charged into a reaction vessel where the amine salt is heated to its decomposition temperature or higher to decompose, thereby obtaining a distillate containing the evolved amine while precipitating the aromatic polycarboxylic acid in the reaction vessel. During the simultaneous distillation and precipitation, the amount of water in the reaction vessel is preferably kept at a predetermined level or higher by feeding water thereinto. The decomposition of the amine salt is stopped when a predetermined amount or higher, preferably 50% or higher, more preferably 90% or higher of the amine salt is decomposed.

The amount of water used in the salt decomposition step varies depending upon kinds of the aromatic polycarboxylic acid and amine being evolved, and is preferably 0.2 to 20 parts by weight, more preferably 0.5 to 5 parts by weight based on one part of the amine salt of aromatic polycarboxylic acid. When the temperature of the salt decomposition step is too low, the decomposition speed of the amine salt is lowered so that the amount of distillate is increased. When the temperature is too high, the evolved amine and aromatic polycarboxylic acid may be further decomposed or undesirably colored. Therefore, the temperature of the salt decomposition step is 50 to 250° C., preferably 120 to 210° C. The pressure in the salt decomposition step varies depending upon the proportions of contents in the reaction vessel at the heating temperature, and is usually −0.1 to 5 MPa·G, preferably 0 to 2 MPa·G. The heat supply can be reduced by decomposing the amine salt while blowing an inert gas such as a nitrogen gas into the reaction vessel.

By the above methods, the amine salt of aromatic polycarboxylic acid is decomposed and the evolved amine is collected by cooling, thereby recovering whole amine used. The recovered amine is purified, if desired, and reused in the salt formation step. Simultaneously with the distillation of the amine, the liberated aromatic polycarboxylic acid is precipitated in the solution. The precipitated aromatic polycarboxylic acid is separated and recovered from the solution by solid-liquid separation methods such as filtration and centrifugation. The recovered crystals may be washed with water to remove impurities attached thereto. The mother liquor and the washings of crystals after the solid-liquid separation may be recycled to the salt formation step to remove the concentrated impurities out of the reaction system. The obtained crystals are dried to obtain a highly pure aromatic polycarboxylic acid.

By decomposing the amine salt in the presence of water as described above, organic impurities such as aromatic tricarboxylic acids and brominated aromatic carboxylic acids, which are relatively difficult to remove in the salt formation step, are almost completely removed. Also, the resultant aromatic polycarboxylic acid is less colored and has increased particle size.

The present invention will be explained in more detail by reference to the following examples which should not be construed to limit the scope of the present invention.

In the following examples and comparative examples, the organic impurities in the raw materials, the amine salts of aromatic dicarboxylic acids and crystals of highly pure aromatic dicarboxylic acids were analyzed by gas chromatography after methyl esterification, and the metal impurities were analyzed by ICP emission spectrometry after wet decomposition.

The degree of coloration was evaluated by 400 nm optical density ($OD_{400}$) measured on an aqueous solution of one gram of sample naphthalenedicarboxylic acid or biphenyldicarboxylic acid in 10 ml aqueous solution of 1N sodium hydroxide using a quartz cell with 10 mm penetration distance. The degree of coloration of the amine salt was evaluated in the same manner as above after vacuum dry at 100° C. for 3 hours. The mean particle diameter was measured by a laser diffraction particle-size analyzer. The recovery was expressed by the ratio of the amount of aromatic dicarboxylic acid in crystals based on the amount of crude aromatic dicarboxylic acid charged as the raw material.

The following abbreviations are used in the examples, comparative examples and Tables.

NDCA: Naphthalenedicarboxylic acid;
NA: Naphthoic acid;
FNA: Formyl naphthoic acid;
TMAC: Trimellitic acid;
Br-NDCA: Brominated naphthalenedicarboxylic acid;
NTCA: Naphthalenetricarboxylic acid;
L.E.: Low-boiling components;
H.E.: High-boiling components;
TEA: Triethylamine;
TMA: Trimethylamine;
DEA: Diethylamine
NDCA.TEA: Naphthalenedicarboxylic acid di(triethylamine) salt;
NDCA.TMA: Naphthalenedicarboxylic acid di(trimethylamime) salt;
NDCA.DEA: Naphthalenedicarboxylic acid di(diethylamine) salt;
NDCA.EA: Naphthalenedicarboxylic acid di(ethylamine) salt;
BPDA: Biphenyldicarboxylic acid;
BPDA IS: Biphenyldicarboxylic acid isomer;
BPDA.TEA: Biphenyldicarboxylic acid di(triethylamine) salt;
BPMA: Biphenylmonocarboxylic acid; and
TA: Terephthalic acid.

EXAMPLE 1

The oxidation product of 2,6-dimethylnaphthalene in the presence of an oxidation catalyst containing a heavy metal and a bromine compound was filtered, washed and then dried to produce a crude 2,6-NDCA shown in Table 1 as a starting material. The crude 2,6-NDCA contained 540 ppm of Co and 2,500 ppm of Mn.

Into a 2-liter three-necked glass flask equipped with a reflux condenser, a stirring device and a temperature-measuring tube, were charged 200 g of the crude 2,6-NDCA shown in Table 1 and 500 g of 10% water-containing ethanol as a solvent. After adding 200 g of TEA (1.07 equivalents based on the acid equivalent of 2,6-NDCA), the contents of the flask was mixed with stirring at a constant temperature of 25° C. for 30 minutes to form amine salt. The resultant slurry containing purified 2,6-NDCA.TEA crystals was filtered through a G2 glass filter, and the crystals on the filter were rinsed with 200 g of acetone to obtain 334 g of 2,6-NDCA.TEA crystals (79.5 % recovery). The chemical composition and the degree of coloration of the obtained crystals are shown in Table 1.

EXAMPLE 2

In the same manner as in Example 1 except that 1,000 g of 20% water-containing acetone were used instead of 500 g of 10% water-containing ethanol, 328 g of 2,6-NDCA.TEA crystals were obtained (78.0 % recovery). The chemical composition and the degree of coloration of the obtained crystals are shown in Table 1.

EXAMPLE 3

In the same manner as in Example 1 except that 1,000 g of 20% water-containing acetonitrile were used instead of 500 g of 10% water-containing ethanol, 235 g of 2,6-NDCA.TEA crystals were obtained (55.9 % recovery). The chemical composition and the degree of coloration of the obtained crystals are shown in Table 1.

TABLE 1

| | Crude 2,6-NDCA | Example 1 | Example 2 | Example 3 |
|---|---|---|---|---|
| Chemical Composition (%) | | | | |
| 2,6-NDCA | 97.610 | 99.750 | 99.908 | 99.885 |
| TMAC | 1.124 | 0.055 | 0.01o | 0.011 |
| FNA | 0.398 | 0.064 | 0.013 | 0.013 |
| NTCA | 0.340 | 0.059 | 0.040 | 0.059 |
| Br-NDCA | 0.283 | 0.042 | 0.021 | 0.026 |
| L.E. | 0.089 | 0.013 | 0.004 | 0.002 |
| H.E | 0.156 | 0.017 | 0.004 | 0.004 |
| Degree of Coloration | | | | |
| $OD_{400}$ | 2.180 | 0.183 | 0.148 | 0.158 |

EXAMPLE 4

In the same manner as in Example 1 except that 1,000 g of 10% water-containing pyridine were used instead of 500 g of 10% water-containing ethanol, 372 g of 2,6-NDCA.TEA crystals were obtained (88.5 % recovery). The chemical composition and the degree of coloration of the obtained crystals are shown in Table 2.

EXAMPLE 5

In the same manner as in Example 1 except that 1,000 g of 10% water-containing tetrahydrofuran were used instead of 500 g of 10% water-containing ethanol, 382 g of 2,6-NDCA.TEA crystals were obtained (90.9 % recovery). The chemical composition and the degree of coloration of the obtained crystals are shown in Table 2.

EXAMPLE 6

In the same manner as in Example 1 except that 1,000 g of 10% water-containing dimethylacetamide were used instead of 500 g of 10% water-containing ethanol, 356 g of 2,6-NDCA.TEA crystals were obtained (84.7 % recovery). The chemical composition and the degree of coloration of the obtained crystals are shown in Table 2.

EXAMPLE 7

In the same manner as in Example 1 except that 500 g of 20% water-containing isopropanol were used instead of 500 g of 10% water-containing ethanol, 355 g of 2,6-NDCA.TEA crystals were obtained (84.4 % recovery). The chemical composition and the degree of coloration of the obtained crystals are shown in Table 2.

TABLE 2

| | Example 4 | Example 5 | Example 6 | Example 7 |
|---|---|---|---|---|
| Chemical Composition (%) | | | | |
| 2,6-NDCA | 99.756 | 99.614 | 99.632 | 99.895 |
| TMAC | 0.035 | 0.155 | 0.132 | 0.015 |
| FNA | 0.047 | 0.074 | 0.074 | 0.015 |
| NTCA | 0.083 | 0.059 | 0.046 | 0.044 |
| Br-NDCA | 0.062 | 0.032 | 0.035 | 0.022 |

TABLE 2-continued

| | Example 4 | Example 5 | Example 6 | Example 7 |
|---|---|---|---|---|
| L.E. | 0.012 | 0.055 | 0.025 | 0.005 |
| H.E | 0.005 | 0.011 | 0.056 | 0.004 |
| Degree of Coloration | | | | |
| $OD_{400}$ | 0.155 | 0.213 | 0.174 | 0.189 |

EXAMPLE 8

Into a 2-liter three-necked glass flask equipped with a reflux condenser, a stirring device and a temperature-measuring tube, were charged 200 g of the crude 2,6-NDCA shown in Table 1 and 400 g of ethanol. After adding 200 g of TEA (1.07 equivalents based on the acid equivalent of 2,6-NDCA), the contents of the flask was mixed with stirring at a constant temperature of 25° C. for 30 minutes to form amine salt. The resultant slurry containing 2,6-NDCA.TEA crystals was filtered through a G2 glass filter, and the crystals on the filter were rinsed with 200 g of acetone to obtain 302 g of 2,6-NDCA. TEA crystals (71.8 % recovery). The chemical composition and the degree of coloration of the obtained crystals are shown in Table 3. The obtained crystals were slightly reduced in purity and colored as compared with Example 1 where ethanol containing 10% water was used as the solvent.

EXAMPLE 9

In the same manner as in Example 8 except that 500 g of α-picoline were used instead of 400 g of ethanol, 340 g of 2,6-NDCA.TEA crystals were obtained (80.9 % recovery). The chemical composition and the degree of coloration of the obtained crystals are shown in Table 3.

EXAMPLE 10

In the same manner as in Example 8 except that 500 g of dimethylacetamide were used instead of 400 g of ethanol, 355 g of 2,6-NDCA.TEA crystals were obtained (84.4 % recovery). The chemical composition and the degree of coloration of the obtained crystals are shown in Table 3.

EXAMPLE 11

In the same manner as in Example 8 except that 400 g of dimethylsulfoxide were used instead of 400 g of ethanol, 328 g of 2,6-NDCA.TEA crystals were obtained (78.0 % recovery). The chemical composition and the degree of coloration of the obtained crystals are shown in Table 3.

EXAMPLE 12

In the same manner as in Example 8 except that 200 g of water were used instead of 400 g of ethanol and the salt formation, filtration and rinsing were performed at 0° C. while cooling with ice, 123 g of 2,6-NDCA.TEA crystals were obtained (29.3 % recovery). The chemical composition and the degree of coloration of the obtained crystals are shown in Table 3. Since only water was used as the solvent for the salt formation, the recovery was lowered.

TABLE 3

|  | Example 8 | Example 9 | Example 10 | Example 11 | Example 12 |
|---|---|---|---|---|---|
| Chemical Composition (%) | | | | | |
| 2,6-NDCA | 99.651 | 99.691 | 99.691 | 99.667 | 99.654 |
| TMAC | 0.088 | 0.078 | 0.078 | 0.079 | 0.085 |
| FNA | 0.078 | 0.061 | 0.061 | 0.082 | 0.078 |
| NTCA | 0.065 | 0.066 | 0.042 | 0.064 | 0.081 |
| Br-NDCA | 0.056 | 0.056 | 0.068 | 0.048 | 0.060 |
| L.E. | 0.041 | 0.023 | 0.025 | 0.025 | 0.021 |
| H.E | 0.021 | 0.025 | 0.035 | 0.035 | 0.021 |
| Degree of Coloration | | | | | |
| $OD_{400}$ | 0.258 | 0.189 | 0.215 | 0.254 | 0.154 |

EXAMPLE 13

Into a 2-liter three-necked glass flask equipped with a reflux condenser, a stirring device and a temperature-measuring tube, were charged 200 g of the crude 2,6-NDCA shown in Table 1 and 1122.8 g of acetone. After adding 401 g of 30 wt. % TMA aqueous solution (1.1 equivalents based on the acid equivalent of 2,6-NDCA), the contents of the flask was mixed with stirring at a constant temperature of 25° C. for 30 minutes to form amine salt. The resultant slurry containing 2,6-NDCA.TMA crystals was filtered through a G2 glass filter, and 10 the crystals on the filter were rinsed with 200 g of acetone to obtain 228 g of 2,6-NDCA.TMA crystals (73.7 % recovery). The chemical composition and the degree of coloration of the obtained crystals are shown in Table 4.

EXAMPLE 14

Into a 2-liter three-necked glass flask equipped with a reflux condenser, a stirring device and a temperature-measuring tube, were charged 200 g of the crude 2,6-NDCA shown in Table 1 and 1000 g of 20 wt. % water-containing acetone. After adding 148.8 g of DEA (1.1 equivalents based on the acid equivalent of 2,6-NDCA), the contents of the flask was mixed with stirring at a constant temperature of 25° C. for 30 minutes to form amine salt. The resultant slurry containing 2,6-NDCA.DEA crystals was filtered through a G2 glass filter, and the crystals on the filter were rinsed with 200 g of acetone to obtain 256 g of 2,6-NDCA.DEA crystals (76.3 % recovery). The chemical composition and the degree of coloration of the obtained crystals are shown in Table 4.

EXAMPLE 15

Into a 2-liter three-necked glass flask equipped with a reflux condenser, a stirring device and a temperature-measuring tube, were charged 200 g of the crude 2,6-NDCA shown in Table 1, 800 g of acetone and 161 g of water. After adding 131.1 g of 70 wt. % EA aqueous solution (1.1 equivalents based on the acid equivalent of 2,6-NDCA), the contents of the flask was mixed with stirring at a constant temperature of 25° C. for 30 minutes to form amine salt. The resultant slurry containing 2,6-NDCA.EA crystals was filtered through a G2 glass filter, and the crystals on the filter were rinsed with 200 g of acetone to obtain 222 g of 2,6-NDCA.EA crystals (73.9 % recovery). The chemical composition and the degree of coloration of the obtained crystals are shown in Table 4.

COMPARATIVE EXAMPLE 1

Into a 2-liter SUS autoclave equipped with a stirring device, a temperature-measuring tube, a pressure filter and a heating medium circulator, were charged the same starting materials in the same charged amounts as in Example 1. The contents of the autoclave were heated to 120° C. and stirred at that temperature for 30 minutes, thereby completely dissolving the contents. At this time, the inner pressure of the autoclave was 0.35 MPa. Then, the resultant solution was cooled to 25° C. over 3 hours and stirred for 30 minutes. The resultant mixture was pressure-filtered at 25° C. and the collected crystals were rinsed with 200 g of acetone, thereby obtaining 316 g of 2,6-NDCA.TEA crystals (75.2 % recovery). The chemical composition and the degree of coloration of the obtained crystals are shown in Table 4.

Although the crude naphthalenedicarboxylic acid was somewhat purified by recrystallization, the use of a pressure reaction vessel was essential and a large quantity of energy was required for the heat dissolution and cooling. Further, the process was complicated and time-consuming.

COMPARATIVE EXAMPLE 2

Into a 2 liter three-necked glass flask equipped with a reflux condenser, a stirring device and a temperature-measuring tube, were charged 200 g of the crude 2,6-NDCA shown in Table 1, 400 g of water and 200 g of TEA. The contents were stirred and completely dissolved. The resultant solution was added with 20 g of activated carbon powder (Wako Junyaku Co., Ltd.), stirred for 30 minutes, and then filtered through a G2 glass filter to remove the activated carbon.

The filtrate was evaporated to dryness by an evaporator, and the crystals obtained were vacuum-dried at 100° C. for 3 hours. The chemical composition and the degree of coloration of the obtained crystals are shown in Table 4. Irrespective of using a large amount of activated carbon, the decoloration was unsatisfactory and the removal of organic impurities was insufficient.

TABLE 4

|  | Example 13 | Example 14 | Example 15 | Comparative Example 11 | Comparative Example 12 |
|---|---|---|---|---|---|
| Chemical Composition (%) | | | | | |
| 2,6-NDCA | 99.883 | 99.855 | 99.867 | 99.804 | 98.530 |
| TMAC | 0.012 | 0.021 | 0.018 | 0.042 | 0.890 |
| FNA | 0.015 | 0.018 | 0.016 | 0.055 | 0.021 |
| NTCA | 0.048 | 0.055 | 0.048 | 0.046 | 0.290 |
| Br-NDCA | 0.032 | 0.032 | 0.028 | 0.042 | 0.110 |
| L.E. | 0.005 | 0.004 | 0.005 | 0.005 | 0.970 |
| H.E | 0.005 | 0.015 | 0.018 | 0.006 | 0.089 |
| Degree of Coloration | | | | | |
| $OD_{400}$ | 0.164 | 0.168 | 0.156 | 0.172 | 0.223 |

EXAMPLE 16

Into 2-liter three-necked glass flask equipped with a reflux condenser, a stirring device and a temperature-measuring tube, were charged 2000 g of respective water-acetone mixed solvents having water contents of 4%, 10%, 30% and 60%. Further, 200 g of the crude 2,6-NDCA shown in Table 1 were charged. After adding 200 g of TEA to the flask, the contents were mixed with stirring for 30 minutes to form amine salt. The resultant slurry containing 2,6-NDCA.TEA crystals was filtered at 25° C. through a G2 glass filter and the crystals on the filter were rinsed with a suitable amount of acetone.

The charged amounts, the amounts of crystals obtained, recovery of the crystals and the chemical compositions of the obtained purified 2,6-NDCA.TEA crystals are collectively shown in Table 5. When the water content was too low, the decoloration was insufficient and the removal of organic impurities was low. On the contrary, when the water content was too high, the recovery of 2,6-NDCA.TEA crystals was low although a high purification effect was obtained.

TABLE 5

| | Water Contents of Mixed Solvents | | | |
|---|---|---|---|---|
| | 4% | 10% | 30% | 60% |
| Charged Amounts (g) | | | | |
| Crude 2,6-NDCA | 200 | 200 | 200 | 200 |
| TEA | 200 | 200 | 200 | 200 |
| Mixed Solvent | | | | |
| Acetone | 1920 | 1800 | 350 | 200 |
| Water | 80 | 200 | 150 | 300 |
| Recovered Crystals (g) | 413 | 397 | 274 | 84 |
| Recovery of NDCA (%) | 99.4 | 94.4 | 65.1 | 19.9 |
| Composition of organic compounds (%) | | | | |
| 2,6-NDCA | 99.566 | 99.855 | 99.931 | 99.931 |
| TMAC | 0.089 | 0.027 | 0.008 | 0.007 |
| FNA | 0.074 | 0.027 | 0.005 | 0.005 |
| NTCA | 0.102 | 0.045 | 0.032 | 0.034 |
| Br-NDCA | 0.055 | 0.033 | 0.020 | 0.021 |
| L.E. | 0.058 | 0.007 | 0.002 | 0.001 |
| H.E | 0.056 | 0.006 | 0.002 | 0.001 |
| Degree of Coloration | | | | |
| $OD_{400}$ | 0.342 | 0.211 | 0.110 | 0.108 |

EXAMPLE 17

Into 200 g of water, 200 g of purified 2,6-NDCA.TEA crystals which were produced in the same manner as in Example 2 were dissolved, and the resultant solution was subjected to precision filtration using a hum filter to remove foreign materials and insolubles.

Into a 1-liter SUS autoclave equipped with a condenser, a stirring device, a pressure filter and an aluminum block heater, were charged the aqueous solution of the amine salt. The solution was heated to 150° C., and the salt decomposition was carried out for 3 hours by feeding water, while maintaining the temperature at 150° C. under stirring, at a feeding rate of 200 g/hr so as to compensate for the distillation loss by feeding water. Then, the reaction mixture was allowed to stand until it was cooled to 100° C., and pressure-filtered to obtain crystals, which were washed with 200 g of water, and then vacuum-dried at 50° C. for 3 hours. As a result, 92.1 g of 2,6-NDCA were obtained. The chemical composition and the degree of coloration of the obtained crystals are shown in Table 6. The obtained highly pure 2,6-NDCA had a large particle size and was sufficient in decoloration and removal of organic impurities.

EXAMPLE 18

In the same manner as in Example 17 except for using 200 g of the purified 2,6-NDCA.TMA obtained in Example 13 in place of 200 g of 2,6-NDCA.TEA, 110.5 g of highly pure 2,6-NDCA were obtained. The chemical composition and the degree of coloration of the obtained crystals are shown in Table 6.

EXAMPLE 19

In the same manner as in Example 17 except for using 200 g of the purified 2,6-NDCA.DEA obtained in Example 14 in place of 200 g of the purified 2,6-NDCA.TEA, 60.6 g of highly pure 2,6-NDCA were obtained. The chemical composition and the degree of coloration of the obtained crystals are shown in Table 6. The yield was lower than those of Examples 17 and 18 using the TEA and TMA salts due to slow decomposition of the amine salt. Also, the particle size was slightly smaller than those using the TEA and TMA salts.

EXAMPLE 20

In the same manner as in Example 17 except for using 200 g of the purified 2,6-NDCA.EA obtained in Example 15 in place of 200 g of the purified 2,6-NDCA.TEA, 50.9 g of highly pure 2,6-NDCA were obtained. The chemical composition and the degree of coloration of the obtained crystals are shown in Table 6. The yield was lower than those of Examples 17 and 18 using the TEA and TMA salts due to slow decomposition of the amine salt. Also, the particle size was slightly smaller than those using the TEA and TMA salts.

TABLE 6

| | Example 17 | Example 18 | Example 19 | Example 20 |
|---|---|---|---|---|
| Chemical Composition (%) | | | | |
| 2,6-NDCA | 99.989 | 99.984 | 99.982 | 99.983 |
| TMAC | 0.000 | 0.000 | 0.000 | 0.000 |
| FNA | 0.008 | 0.012 | 0.015 | 0.012 |
| NTCA | 0.000 | 0.000 | 0.000 | 0.000 |
| Br-NDCA | 0.000 | 0.000 | 0.000 | 0.000 |
| L.E. | 0.002 | 0.001 | 0.001 | 0.003 |
| H.E | 0.001 | 0.003 | 0.002 | 0.002 |
| Co + Mn (ppm) | <5 | <5 | <5 | <5 |
| Mean Particle Diameter (μm) | 125 | 132 | 88 | 75 |
| Degree of Coloration | | | | |
| $OD_{400}$ | 0.084 | 0.079 | 0.088 | 0.089 |

EXAMPLE 21

Into a 2-liter three-necked glass flask equipped with a reflux condenser, a stirring device and a temperature-measuring tube, were charged 200 g of the crude 2,6-NDCA shown in Table 1, 160 g of acetone and 120 g of $H_2O$ (water content of mixed solvent: 42.8%). After adding 200 g of TEA, the contents of the flask was mixed with stirring at a constant temperature of 25° C. for 30 minutes to form amine salt. Then, 644 g of acetone were added to the flask, and the contents of the flask were mixed with stirring for 30 minutes, thereby further precipitating 2,6-NDCA.TEA crystals. The resultant slurry containing 2,6-NDCA.TEA crystals was filtered through a G2 glass filter, and the crystals on the filter were rinsed with 300 g of acetone, thereby obtaining 412 g of purified 2,6-NDCA.TEA crystals (98.0% recovery). The chemical composition and the degree of coloration of the obtained crystals are shown in Table 7. In this Example, the formation of amine salt was completed by using the solvent having a high water content and the crystals were precipitated by the addition of acetone. The precipitated crystals were less colored although the recovery was high.

Into 200 g of water, 200 g of purified 2,6-NDCA.TEA crystals were dissolved, and the resultant solution was subjected to precision filtration using a 1 μm filter to remove foreign materials and insolubles.

Into a 1-liter SUS autoclave equipped with a condenser, a stirring device, a pressure filter and an aluminum block heater, were charged the aqueous solution of the amine salt. The solution was heated to 200° C., and the salt decomposition was carried out for 3 hours by feeding water, while maintaining the temperature at 200° C. under stirring, at a feeding rate of 200 g/hr so as to compensate for the distillation loss by feeding water. Then, the reaction mixture was allowed to stand until it was cooled to 100° C. and filtered to obtain crystals, which were washed with water and then vacuum-dried. As a result, 93.3 g of highly pure 2,6-NDCA were obtained. The chemical composition and the degree of coloration of the obtained crystals are shown in Table 7.

TABLE 7

|  | 2,6-NDCA.TEA | 2,6-NDCA |
| --- | --- | --- |
| Chemical Composition (%) |  |  |
| 2,6-NDCA | 99.871 | 99.976 |
| TMAC | 0.015 | 0.000 |
| FNA | 0.018 | 0.012 |
| NTCA | 0.050 | 0.000 |
| Br-NDCA | 0.021 | 0.000 |
| L.E. | 0.013 | 0.008 |
| H.E | 0.002 | 0.004 |
| Co + Mn (ppm) | — | <5 |
| Mean Particle Diameter (μm) | — | 142 |
| Degree of Coloration $OD_{400}$ | 0.158 | 0.120 |

EXAMPLE 22

Into a 3-liter three-necked glass flask equipped with a reflux condenser, a stirring device and a temperature-measuring tube, were charged 250 g of the crude 2,6-NDCA shown in Table 1, 1,800 g of acetone and 200 g of $H_2O$. After adding 250 g of TEA, the contents of the flask were mixed with stirring for 30 minutes to form amine salt. After cooling to 10° C., the resultant slurry containing 2,6-NDCA.TEA crystals was filtered through a G2 glass filter, and the crystals on the filter were rinsed with 400 g of acetone, thereby obtaining 408 g of first 2,6-NDCA.TEA crystals before recrystallization (96.1% recovery).

Into a 2-liter SUS autoclave equipped with a stirring device, a temperature-measuring tube, a pressure filter and a jacket, were charged 400 g of 2,6-NDCA.TEA crystals obtained above, 800 g of acetone and 200 g of water. The contents of the autoclave were heated to 90° C. while circulating hot water through the jacket, were completely dissolved at 90° C. under stirring for 30 minutes. At this time, the inner pressure of the autoclave was 0.25 MPa. Then, the resultant solution was cooled to 25° C. over 3 hours, and then pressure-filtered at 25° C. The obtained crystals were rinsed with 200 g of acetone to obtain second 312 g of 2,6-NDCA.TEA crystals after recrystallization (78.0% recovery).

In the same manner as in Example 17 except for using 200 g of the 2nd 2,6-NDCA.TEA as the starting material, highly pure 2,6-NDCA was obtained. The chemical composition and the degree of coloration of the obtained crystals are shown in Table 8.

By recrystallization, before the salt decomposition step, of the 2,6-NDCA.TEA, extremely pure 2,6-NDCA was obtained.

TABLE 8

|  | First 2,6-NDCA · TEA | Second 2,6-DNCA · TEA | 2,6-NDCA |
| --- | --- | --- | --- |
| Chemical Composition (%) |  |  |  |
| 2,6-NDCA | 99.810 | 99.988 | 99.995 |
| TMAC | 0.045 | 0.001 | 0.000 |
| FNA | 0.055 | 0.000 | 0.000 |
| NTCA | 0.037 | 0.004 | 0.000 |
| Br-NDCA | 0.038 | 0.003 | 0.000 |
| L.E. | 0.007 | 0.002 | 0.002 |
| H.E | 0.008 | 0.002 | 0.003 |
| Co + Mn (μm) | — | — | <5 |
| Mean Particle Diameter (μm) | — | — | 125 |
| Degree of Coloration |  |  |  |
| $OD_{400}$ | 0.225 | 0.030 | 0.020 |

EXAMPLE 23

In the same manner as in Example 2 except for adding 2.0 g of powdery activated carbon (produced by Wako Junyaku Co., Ltd.), 328 g of 2,6-NDCA.TEA were obtained (78.0% recovery). The chemical composition and the degree of coloration of the obtained crystals are shown in Table 9.

In the same manner as in Example 17, highly pure 2,6-NDCA having the chemical composition and the degree of coloration as shown in Table 9 was obtained by using the purified 2,6-NDCA.TEA obtained above. r 10 Since the treatment by powdered activated carbon was made in the salt formation, the resultant 2,6-NDCA TEA was extremely pure.

TABLE 9

|  | 2,6-NDCA.TEA | 2,6-NDCA |
| --- | --- | --- |
| Chemical Composition (%) |  |  |
| 2,6-NDCA | 99.922 | 99.998 |
| TMAC | 0.010 | 0.000 |
| FNA | 0.000 | 0.000 |
| NTCA | 0.041 | 0.000 |
| Br-NDCA | 0.025 | 0.000 |
| L.E. | 0.001 | 0.001 |
| H.E | 0.001 | 0.001 |
| Co + Mn (ppm) | — | <5 |
| Mean Particle Diameter (μm) | — | 120 |
| Degree of Coloration ($OD_{400}$) | 0.042 | 0.031 |

EXAMPLE 24

Into 2,000 g of water, were dissolved 2,000 g of purified 2,6-NDCA.TEA which were obtained in the same manner as in Example 2 except for scaling up by 10 times. The resultant solution was filtered through a 1 μm filter to remove foreign materials and insolubles. Separately, a jacketed stainless steel reaction tube having an inner diameter of 13 mm was filled with 5 g of granular activated carbon (produced by Kuraray Co., Ltd.) and heated to 80° C. Then, the solution of 2,6-NDCA.TEA was passed through the reaction tube at a rate of 100 g/hr while maintaining the reaction tube at 80° C. After the whole solution was passed, a part of the effluent was dried under reduced pressure and analyzed. The results of analysis showed that the effluent was aqueous solution of 2,6-NDCA.TEA having the chemical composition and the degree of coloration as shown in Table 10. Using 400 g of the aqueous solution of 2,6-NDCA.TEA, highly pure 2,6-NDCA having the chemical composition and the degree of coloration as shown in Table 10 was obtained by the salt decomposition in the same manner as in Example 17.

TABLE 10

|  | 2,6-NDCA.TEA | 2,6-NDCA |
| --- | --- | --- |
| Chemical Composition (%) | | |
| 2,6-NDCA | 99.946 | 99.998 |
| TMAC | 0.012 | 0.000 |
| FNA | 0.000 | 0.000 |
| NTCA | 0.020 | 0.000 |
| Br-NDCA | 0.010 | 0.000 |
| L.E. | 0.008 | 0.001 |
| H.E | 0.004 | 0.001 |
| Co + Mn (ppm) | | <5 |
| Mean Particle Diameter ($\mu$m) | | 124 |
| Degree of Coloration ($OD_{400}$) | 0.035 | 0.028 |

EXAMPLE 25

The oxidation product of 4-ethyl-4'-formyl biphenyl in the presence of an oxidation catalyst containing a heavy metal and a bromine compound was filtered, washed and then dried to produce a crude 4,4'-BPDA shown in Table 11 as a starting material.

Into a 2-liter three-necked glass flask equipped with a reflux condenser, a stirring device and a temperature-measuring tube, were charged 200 g of the crude 4,4'-BPDA shown in Table 11 and 500 g of 5% water-containing acetone as a solvent. After adding 220 g of TEA (1.1 equivalents based on the acid equivalent of 4,4'-BPDA), the contents of the flask was mixed with stirring at a constant temperature of 10° C. for 30 minutes to form amine salt. The resultant slurry containing purified 4,4'-BPDA.TEA crystals was filtered through a G2 glass filter, and the crystals on the filter were rinsed with 200 g of acetone to obtain 298 g of 4,4'-BPDA.TEA crystals (78.0 % recovery). The chemical composition and the degree of coloration of the obtained crystals are shown in Table 11.

EXAMPLE 26

In the same manner as in Example 25 except that 5 wt. % water-containing pyridine was used instead of 500 g of 5 wt. % water-containing acetone, 246 g of 4,4'-BPDA.TEA crystals were obtained (64.4 % recovery). The chemical composition and the degree of coloration of the obtained crystals are shown in Table 11.

EXAMPLE 27

In the same manner as in Example 25 except that 500 g of N,N-dimethyl acetamide were used instead of 500 g of 5 wt. % water-containing acetone, 321 g of 4,4'-BPDA.TEA crystals were obtained (84.0 % recovery). The chemical composition and the degree of coloration of the obtained crystals are shown in Table 11.

TABLE 11

|  | Crude 4,4'-BPDA | Example 25 | Example 26 | Example 27 |
| --- | --- | --- | --- | --- |
| Chemical Composition (%) | | | | |
| 4,4'-BPDA | 96.99 | 99.936 | 99.931 | 99.895 |
| BPDAIS | 0.38 | 0.006 | 0.007 | 0.025 |
| BPMA | 0.18 | 0.015 | 0.031 | 0.038 |
| TA | 1.75 | 0.004 | 0.003 | 0.005 |
| L.E. | 0.45 | 0.012 | 0.014 | 0.012 |
| H.E | 0.25 | 0.027 | 0.014 | 0.025 |
| Degree of Coloration | | | | |
| $OD_{400}$ | 1.589 | 0.189 | 0.216 | 0.359 |

EXAMPLE 28

In the same manner as in Example 25 except that 400 g of a-picoline were used instead of 500 g of 5 wt. % water-containing acetone, 245 g of 4,4'-BPDA.TEA crystals were obtained (64.1 % recovery). The chemical composition and the degree of coloration of the obtained crystals are shown in Table 12.

EXAMPLE 29

In the same manner as in Example 25 except that 2 g of powdered activated carbon (Wako Junyaku Co., Ltd.) were added together with the solvent in the salt formation step, 302 g of 4,4'-BPDA.TEA crystals were obtained (79.1 % recovery). The chemical composition and the degree of coloration of the obtained crystals are shown in Table 12.

EXAMPLE 30

Into 200 g of water, 200 g of purified 4,4'-BPDA.TEA crystals produced in Example 25 were dissolved, and the resultant solution was subjected to precision filtration using a 1 $\mu$m filter to remove foreign materials and insoluble metals.

Into a 1-liter SUS autoclave equipped with a condenser, a stirring device, a pressure filter and an aluminum block heater, were charged the aqueous solution of the amine salt. The solution was heated to 150° C., and the salt decomposition was carried out for 3 hours by feeding water, while maintaining the temperature at 150° C. under stirring, at a feeding rate of 200 g/hr so as to compensate for the distillation loss by feeding water. Then, the reaction mixture was allowed to stand until it was cooled to 100° C., and pressure-filtered to obtain crystals, which were washed with 200 g of water, and then vacuum-dried at 50° C. for 3 hours. As a result, 100.3 g of 4,4'-BPDA were obtained. The chemical composition and the degree of coloration of the obtained crystals are shown in Table 12. The obtained highly pure 4,4'-BPDA had a large particle size and was sufficient in decoloration and removal of organic impurities.

EXAMPLE 31

Using 200 g of the 4,4'-BPDA.TEA obtained in Example 29, the same procedures as in Example 30 were repeated to obtain 98.8 g of 4,4'-BPDA. The chemical composition and the degree of coloration of the obtained crystals are shown in Table 12. 4,4'-BPDA with much higher purity was obtained by the treatment with activated carbon.

TABLE 12

|  | Example 28 | Example 29 | Example 30 | Example 31 |
|---|---|---|---|---|
| Chemical Composition (%) | | | | |
| 4,4'-BPDA | 99.891 | 99.937 | 99.994 | 99.998 |
| BPDMS | 0.012 | 0.015 | 0.000 | 0.000 |
| BPMA | 0.034 | 0.008 | 0.093 | 0.000 |
| TA | 0.007 | 0.004 | 0.000 | 0.000 |
| L.E. | 0.024 | 0.008 | 0.001 | 0.001 |
| H.E | 0.032 | 0.028 | 0.002 | 0.001 |
| Co + Mn (ppm) | — | — | <5 | <5 |
| Mean Particle Diameter ($\mu$m) | — | — | 115 | 116 |
| Degree of Coloration | | | | |
| $OD_{400}$ | 0.389 | 0.068 | 0.167 | 0.043 |

In accordance with the present invention, purified amine salts of aromatic polycarboxylic acids are obtained in the form of crystals by simply mixing crude aromatic polycarboxylic acids with amines in a solvent at ordinary temperature under ordinary pressure. By subjecting aqueous solutions of the amine salts to decomposition, corresponding highly pure aromatic polycarboxylic acids with less coloration are obtained. The process of the present invention is effectively applicable, in particular, to naphthalenedicarboxylic acids and biphenyldicarboxylic acids which are sparingly soluble in water.

The process for the production of highly pure aromatic polycarboxylic acid according to the present invention has the following advantages.

(1) Since crude aromatic polycarboxylic acids are purified by merely mixing them with amines with stirring in the presence of a solvent at ordinary temperature under ordinary pressure, the process design and operations are simplified.

(2) Since the salt formation includes no step of complete dissolution, the recovery of amine salts is freely controlled, and the recovery as high as 95% or more can be easily achieved.

(3) By using recrystallization or activated carbon treatment in combination with the process of the present invention, the degree of purification is further enhanced.

(4) By thermally decomposing purified amine salts of aromatic polycarboxylic acids in the presence of water, highly pure and less colored aromatic polycarboxylic acids having sufficiently large crystal size are obtained.

(5) Since amines and solvents used can be completely recovered, the amount of wastes can be reduced.

Accordingly, in accordance with the present invention, highly pure, less colored aromatic polycarboxylic acids are produced by simple procedures at low costs. The process of the present invention is highly advantageous to industrial applications and is of extreme industrial importance.

What is claimed is:

1. A process for producing a highly pure aromatic polycarboxylic acid, the process comprising a salt formation step of forming a purified crystalline amine salt by mixing crude aromatic polycarboxylic acid with an aliphatic amine and/or an alicyclic amine in the presence of a solvent containing at most 80% by weight of water, under conditions wherein a substantial part of the amine salt being formed immediately precipitates after formation of the amine salt, thereby preventing the amine salt from completely dissolving in the solvent.

2. The process according to claim 1, further comprising a salt decomposition step of dissolving the amine salt of aromatic polycarboxylic acid into water and subsequently decomposing the amine salt of aromatic polycarboxylic acid into aromatic polycarboxylic acid.

3. The process according to claim 2, the amine salt is decomposed under heating.

4. The process according to claim 1, wherein the aromatic polycarboxylic acid is naphthalenedicarboxylic acid or biphenyldicarboxylic acid.

5. The process according to claim 1, wherein the aliphatic amine is a tertiary amine.

6. The process according to claim 5, wherein the tertiary amine is triethylamine and/or trimethylamine.

7. The process according to claim 1, wherein the solvent used in the salt formation step is a mixed solvent comprising water and a water-soluble organic solvent.

8. The process according to claim 7, wherein the water-soluble organic solvent is at least one solvent selected from the group consisting of acetone, acetonitrile, pyridines, alcohols having 3 or less carbon atoms, dimethylacetamide and dimethylformamide.

9. The process according to claim 8, wherein the water-soluble organic solvent is at least one solvent selected from the group consisting of acetone, pyridine and picoline.

10. The process according to claim 7, wherein the water content of the mixed solvent is 1 to 80% by weight.

11. The process according to claim 1, wherein the salt formation step is carried out at 0 to 70° C.

12. The process according to claim 1, wherein the amine salt is treated with activated carbon in the salt formation step.

13. The process according to claim 1, wherein the amine salt precipitated in the salt formation step is then dissolved in a solvent and then recrystallized from the solvent.

14. The process according to claim 1, wherein the amine salt precipitated in the salt formation step is dissolved in water, treated with activated carbon, and subjected to the salt decomposition step.

15. The process according to claim 1, wherein in the salt formation step a slurry containing crystals of the amine salt is produced.

16. The process according to claim 1, wherein the conditions under which a substantial part of the amine salt precipitates include the addition of a water-soluble organic solvent such that the amine salt precipitates.

17. The process according to claim 1, wherein amount of solvent in the salt formation step is 3–30 parts by weight based on one part by weight of the crude aromatic polycarboxylic acid.

18. The process according to claim 1, wherein the salt formation step is performed at a temperature of below 50° C.

19. The process according to claim 1, wherein the amount of water in the solvent is 5–50% by weight.

20. The process according to claim 1, wherein the salt formation step is performed at a temperature of 10 to 50° C.

21. The process according to claim 20, wherein the salt formation step is performed under a pressure of at most 1 Mpa·G.

22. The process according to claim 1, wherein the salt formation step is performed under a pressure of at most 1 Mpa·G.

* * * * *